United States Patent
Kennedy et al.

(10) Patent No.: US 7,045,138 B2
(45) Date of Patent: May 16, 2006

(54) COMPOSITION FOR MITIGATION OF INSECTS AND/OR MOLLUSCA

(75) Inventors: John Wayne Kennedy, Gambrills, MD (US); Patrick Kennedy, Brenkinridge, TX (US)

(73) Assignee: American Natural Technology Sciences, Inc., Salt Lake City, UT (US)

( * ) Notice: Subject to any disclaimer, the term of this patent is extended or adjusted under 35 U.S.C. 154(b) by 560 days.

(21) Appl. No.: 09/793,014

(22) Filed: Feb. 26, 2001

(65) Prior Publication Data

US 2002/0010156 A1  Jan. 24, 2002

Related U.S. Application Data

(60) Provisional application No. 60/219,309, filed on Jul. 19, 2000.

(51) Int. Cl.
- A01N 25/32 (2006.01)
- A01N 59/14 (2006.01)
- A01N 65/00 (2006.01)

(52) U.S. Cl. .................. 424/406; 424/84; 424/405; 424/408; 424/409; 424/410; 424/417; 424/418; 424/419; 424/420; 424/421; 424/438; 424/535; 424/750; 424/761; 424/778; 424/660; 514/65; 514/703; 514/739

(58) Field of Classification Search .................. 424/84, 424/405–408, 409, 41, 417–421, 442, 438, 424/535, 750, 761, 778; 514/65, 703, 739
See application file for complete search history.

(56) References Cited

U.S. PATENT DOCUMENTS

| | | | |
|---|---|---|---|
| 3,350,264 A | 10/1967 | De Lisle | 167/14 |
| 4,049,460 A | 9/1977 | Broadbent | 106/15 |
| 4,075,783 A | 2/1978 | Burden et al. | 47/1.41 |
| 4,363,798 A * | 12/1982 | D'Orazio | 424/84 |
| 4,855,133 A | 8/1989 | Kamei et al. | 424/84 |
| 4,996,053 A | 2/1991 | Hatcher | 424/410 |
| 5,071,659 A | 12/1991 | Shumaker | 426/1 |
| 5,118,506 A | 6/1992 | Eichoefer | 424/196.1 |
| 5,198,467 A | 3/1993 | Milks | 514/553 |
| 5,223,270 A | 6/1993 | Jones | 424/659 |
| 5,310,489 A * | 5/1994 | Sharif | 252/8.551 |
| 5,480,638 A | 1/1996 | Erwin | 424/84 |
| 5,575,996 A | 11/1996 | Erwin | 424/84 |
| 5,607,682 A * | 3/1997 | Wolfe et al. | 424/405 |
| 5,830,512 A | 11/1998 | Vrba | 424/724 |
| 5,914,105 A | 6/1999 | Barcay et al. | 424/84 |

FOREIGN PATENT DOCUMENTS

EP  0254257  * 1/1988

OTHER PUBLICATIONS

Moore Connecticut Experiment Station Bulletin No. 717 75:4566 Chemical Control of German Cockroaches in Urban Apartments 1971:404566.*

Morrison Feeds & Feeding pp 515,518,,,,,1957.*

* cited by examiner

Primary Examiner—Neil S. Levy
(74) Attorney, Agent, or Firm—Jack Schwartz & Associates

(57) ABSTRACT

A composition including a bait and a borate is used to mitigate a population of target insects and/or mollusca. The composition may include attractive by-products of agriculture and manufacturing with or without semiochemicals or biopesticides prepared as point source units (such as pellets or microcapsules). The by-products attract insects and/or mollusca to a food source for the purpose of mitigating the target organism. The bait is combined with borates and is pelletized and/or encapsulated into micron size particles. The pelletized and/or encapsulated particles are broadcast (spread) over areas infested with the target insect. The insects ingest the composition and regurgitate the composition to the remainder of the insect population. Significant mitigation of the population of the target insects results with little to no effect on the environment. The composition is also passed on to the next generation due to cannibalism of the target insects. A feed through process wherein the composition is fed to an animal and is contained in the manure of the animal deposited as a point source location. The composition is either mixed in with the food of the animal or placed directly in the gut of the animal using a ball and gun method. The target insects are attracted to the manure and upon ingesting the manure, ingest the composition and are dispatched.

18 Claims, No Drawings

COMPOSITION FOR MITIGATION OF INSECTS AND/OR MOLLUSCA

REFERENCE TO RELATED APPLICATIONS

This is a non-provisional application based on U.S. Provisional Application Ser. No. 60/219,309 filed Jul. 19, 2000.

BACKGROUND OF THE INVENTION

1. Field of the Invention

The present invention relates to pesticides and molluscacides for mitigating a population of insects and/or mollusca within a target area and, more particularly, to a composition using baits in an outdoor environment for mitigating populations of insects and/or mollusca, especially Fire Ants, the composition including borates or borates and diatomaceous earth with an attractant in a powdered, pelletized, encapsulated or other form able to act as a bait station.

2. Description of the Prior Art

Numerous pesticide and molluscacide formulations have been provided in the prior art. Historically, sprays and baits have been used to mitigate populations of insects and/or mollusca using chemicals that are toxic to humans and the environment. Examples of such sprays and baits used to mitigate the population of Fire Ants include Dursban®, Amdro® and Mirex® which have fallen into disfavor with both the Environmental Protection Agency (EPA) and the general public. Use of these sprays and baits are now prohibited or restricted by the EPA. Some laboratory studies using borates (usually boric acid) and sugar water and other simple components as baits are published for indoor use against cockroaches and other indoor pests. However, no comprehensive studies using borates or borates and diatomaceous earth (DE) incorporated into pellets, powders or encapsulated for use as a point source, such as saturating corn cob grits or other food source particles for broadcast over an area for control of insects and/or mollusca as disclosed by the present invention have been performed. The use of specific formulations of borates, such as sodium and/or calcium salts, with effective baits and either with or without diatomaceous earth have not been reported. Vermifuge aids in insect control using a feed-through and/or a bolus method.

U.S. Pat. No. 3,350,264 issued to de Lisle describes a process utilizing diatomaceous earth (DE) and U.S. Pat. No. 3,617,298 issued to Otto A. Kohl suggests the incorporation of DE into cattle feed at a level of 0.1 percent to 1.0 percent total weight of the cattle feed. DE in the cattle feed is not absorbed into the stomach of the animal to any extent when ingested. This is because the structure of DE is primarily silicon dioxide and other solid minerals that are not broken down within the gut of the cattle and therefore cannot pass through the stomach or intestinal walls. Thus, the DE passes through the stomach and intestines of the cattle with the undigested food and is combined into the manure of the cattle. According to de Lisle, the DE leaves the body of the cattle with the manure and affects the development of flies which are attracted to and eat the manure. These patents are only concerned with flies affecting cattle.

While these processes may be suitable for the particular purpose to which they address, they would not be as suitable for the purposes of the present invention as heretofore described.

It is therefore desired to provide a composition for mitigating the populations of insects and/or mollusca. It is further desirable to provide a composition for mitigating the populations of insects and/or mollusca including an attractant combined with either borates (including boric acid) or borates and DE, botanical insecticides may also be used. It is yet further desirable to provide a composition for mitigating the populations of insects and/or mollusca which is formulated in any or all of powder, granular (pelletized), bait station or encapsulated form. It is even further desirable to provide a composition for mitigating the populations of insects and/or mollusca able to attract a target pest to a point source for the purpose of mitigating the pest. It is still further desirable to provide a composition for mitigating the populations of insects and/or mollusca in which the point sources of the composition for attracting the target insects and/or mollusca are distributed in a spaced relation near and about the area to be treated. It is yet further desirable to provide a composition for mitigating the populations of insects and/or mollusca which is able to attract insect pests such as face flies, horn flies, house flies, fire ants, etc. and mollusca to point sources such as cattle manure laced with feed-through or bolus pesticides particularly borates or borates and DE. It is even further desirable to provide a composition for mitigating the populations of insects and/or mollusca including a slow acting pesticide that allows any insects and/or mollusca attracted thereto to carry the composition back to the colony or other living space and affect the entire population thereby mitigating generations of the insects and/or mollusca.

SUMMARY OF THE INVENTION

The present invention relates to pesticides and molluscacides for mitigating a population of insects and/or mollusca within a target area and, more particularly, to a composition using baits in broadcast treatments for mitigating the populations of insects and/or mollusca, especially Fire Ants, the composition including an attractant and borates or borates and DE in a powdered, pelletized, encapsulated, powder or bait station form.

It is a primary object of the present invention to provide a composition for mitigating insects and/or mollusca that will overcome the shortcomings of prior art devices and add new means of mitigation of such pests in an environmentally friendly and efficacious manner.

Another object of the present invention is to provide a composition for mitigating insects and/or mollusca which is able to mitigate a population of insects and/or mollusca, especially Fire Ants, within a target area while causing little to no infringement on persons or the non-target environment within the treatment area.

A further object of the present invention is to provide a composition for mitigating insects and/or mollusca which has a low toxicity profile to both the environment and humans.

A yet further object of the present invention is to provide a composition for mitigating insects and/or mollusca including borates or borates and diatomaceous earth combined with an attractant when used in broadcast applications to lower the impact of highly destructive pests such as Fire Ants and fruit flies such as the Med fruit fly, the oriental fruit fly, the Mexican fruit fly and others.

A still further object of the present invention is to provide a composition for mitigating insects and/or mollusca which is able to pass through the digestive tract of an animal and be deposited in the manure of the animal as a point source in the target area for attracting such insects as the fire ant. The composition is able to mitigate any insects infesting the gut of the animal. The deposited manure contains the borates or borates and diatomaceous earth in amounts high enough to mitigate any pest such as the fire ant and/or flies that affect cattle such as the face fly, horn fly or house fly, the same principle applying to other animals.

An even further object of the present invention is to provide a composition for mitigating insects and/or mollusca including diatomaceous earth combined with the borates for mitigating insects in the gut of livestock that cause loss of production of milk or animal weight. The vermifuge principle using borates or borates and diatomaceous earth is non-toxic to the animal.

A still further object of the present invention is to provide a composition for mitigating insects and/or mollusca using borates or borates and diatomaceous earth which is applied to the coat (hair or fur) of the animal, the composition being applied using a dust or spray or other means thereby mitigating pests on the outside (skin) of the animal.

A yet further object of the present invention is to provide a composition for mitigating insects and/or mollusca in either pelletized, encapsulated or other form ingested or carried by an insect and fertilize the ground on which it is deposited thereby increasing the fertility and production of the ground.

An even further object of the present invention is to provide a composition for mitigating insects and/or mollusca which, when combined in the feed of an animal or contained within a bolus, is able to mitigate parasites and/or other harmful organisms within the gut of the animal upon ingestion thereby improving the health and increasing the production of the animal.

Another object of the present invention is to provide a composition for mitigating insects and/or mollusca that is simple and easy to use, has no complex or toxic chemicals or components, meets requirements for organic farming and will not adversely affect man or the environment.

A still further object of the present invention is to provide a composition for mitigating insects and/or mollusca that is economical in cost to manufacture, wherein the components are readily available through mining or are by-products of the dairy or other industries which produce naturally occurring components.

Additional objects of the present invention will appear as the description proceeds.

A composition including a bait and a borate is used to mitigate a population of target insects and/or mollusca is disclosed by the present invention. The composition may include a bait/attractant that is a by-product of agriculture and manufacturing with or without semiochemicals or biopesticides and is prepared as point source units (such as pellets, powder, microcapsules, etc.). The by-products of natural production or artificial baits attract insects and/or mollusca to a food source for the purpose of mitigating the target organism. The bait is combined with borates and is in a powder, pelletized and/or encapsulated form producing micron size particles or used in a bait station. The composition may further include diatomaceous earth. The pelletized, encapsulated or powder particles are broadcast (spread) over areas infested with the target insect. The insects are attracted to specific point sources by the bait or semiochemical and ingest the active pesticide. Insects of many types consume the composition and regurgitate the composition to young stages and the queen of the insect population. Significant mitigation of the population of the target insects results with little to no effect on the environment. The composition is thereby passed on to the next generation due to cannibalism of some species of the target insects.

A feed through process can also be used wherein the composition of the borate or borate and diatomaceous earth is fed to an animal and is contained in the manure of the animal deposited as a point source location. The composition is either mixed in with the food of the animal or placed directly in the gut of the animal using a ball and gun method. The target insects are attracted to the manure and upon ingesting the manure, ingest the composition and are dispatched. The Fire Ant has never been listed as a target pest and the use of borates or borate and diatomaceous earth have neither been disclosed nor suggested.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

DETAILED DESCRIPTION OF THE PREFERRED EMBODIMENT

Boric acid has been traditionally used as a test material when determining efficacy of certain classes of pesticides. The boric acid has usually been used with sugars only or in some combination with protein. Disodium octoborate tetrahydrate (DOT) has been used in formulations or by itself for control of house hold pests such as coach roaches, ants, termites and other urban pests inside of structures. However, neither DOT nor boric acid have been used in formulations with baits in pelletized and/or encapsulized form for broadcast (spreading) treatment over outside structures for the purpose of mitigating pest populations as disclosed by the present invention.

Boric acid has no water molecules attached (dehydrated) thereto. However, DOT and other borates including sodium and calcium salts may be in hydrated salts, meaning that the molecular structure locks up water molecules therein. Therefore, the name disodium octoborate tetrahydrate means that there are four water molecules locked up in the DOT molecule.

Data and study indicate that the hydrated form of the borates including DOT and other salts including calcium are believed to be more acceptable to insects and/or mollusca than boric acid because of the presence of the "locked up" water in the molecular structure. Furthermore, studies performed on the composition of the present invention conclude that moist baits are more readily accepted by the fire ant, for example, than dry baits. However, spreading moist or wet baits is impractical when the main purpose is to broadcast (spread) the bait through an application device by air or ground. Therefore, the present invention is directed toward test formulations which are hydrophilic (water attracting) baits with hydrated borates. Certain hydrophilic compounds acceptable to the EPA are commercially available to add to the "water attraction" nature of the proposed formulations. The present invention includes a unique process of combining baits and DOT or other salts of the borates that have good handling characteristics and can be broadcast by air or ground. Many granulating or "point source" processes are acceptable. The efforts in developing a superior formula in accordance with the present invention were therefore directed toward the use of DOT rather than boric acid.

Furthermore, other hydrated borate salts prove to be much more efficient in bait formulations than boric acid, including calcium borate.

The composition of the present invention includes granular (pelletized) and/or encapsulated and/or powdered by-products of agriculture and/or manufacture in a specially prepared composition. The composition uses food attractants with borates or borates and diatomaceous earth. The composition may also combine the food attractants with biopesticides for broadcast treatment over an area for mitigation of insects or mollusca outside structures. Distribution of the composition may be accomplished using broadcast treatment (spreading) and/or feed through to establish point sources for attracting the insects and/or mollusca to manure containing the composition for the purpose of pest mitigation.

The encapsulation processes utilizing products such as whey, which is hydrophilic, readily breaks down over a few days and is attractive to insects such as the Fire Ant, are incorporated in the present invention. Whey contains lactose and dairy proteins that are attractive to a broad range of insects, including Fire Ants. Other chemicals used in encapsulation may be used in addition to a hydrophilic substance if the encapsulating material does not absorb water naturally. Testing of the compositions and methods of the present invention show that insects accept the proposed ingredients in the dry bait with no reluctance. The dry bait becomes moistened and has proven to be more attractive and thus, more effective.

Laboratory experiments and small-scale field research have demonstrated the efficacy of the composition against Fire Ants using baits with varying levels of success depending primarily on the bait composition. The inventors "Mother's Milk" theory has proved most successful. The variability of components of several baits has provided a new concept bait that has demonstrated superior results. It incorporates a new and untested theory involving components that mimic the nutritional requirements of animals, including insects. The basic chemistry involves a proportional amount of all necessary building blocks a female of the species requires to reproduce. The proportions of proteins, fats, carbohydrates and sugars are almost common among all animals, including insects.

The inventors have experimented with several combinations of the basic components and have discovered that "Mother's Milk" in the form of whey is attractive to several females in several species for the same basic reason. The proportion of the proteins, fats, carbohydrates and sugars are all required and the animal can then reconfigure or reduce each component to satisfy the individual need of that particular species.

The experiments and research also considered the effectiveness of the composition under differing environmental conditions such as temperature, humidity, rainfall, sunshine, etc. To demonstrate the Inventors theory, the composition was graded on acceptability and used in combinations having different % weight ratios for the various components to determine the most effective combination for the composition while also considering economic feasibility. The composition includes several proportions of proteins, sugars, etc. as an attractant combined with borates or borates and diatomaceous earth. Disodium octoborate tetrahydrate (DOT) is the primary borate included in the composition testing and the effectiveness of the combinations of baits and active ingredients tested. All of the compositions tested with DOT incorporated into the formulation were acceptable to varying degrees. The most successful being the combination with the "Mother's Milk" whey which contained the proportions found in cows milk.

EXAMPLE

A superior bait and borate combination using whey, a by-product of dairy production, combined with disodium octoborate tetrahydrate (DOT) was prepared and tested extensively in varying environmental conditions. In these tests, the granulated (pellitized) and powdered whey proved to be an exceptional attractant and the DOT demonstrated a high degree of control. The product demonstrated superior efficacy at five to six days and repeat applications every ten days replicated three times demonstrated complete control.

DOT is a slow acting insecticide. The slow acting nature of the DOT provides a time period between the taking of the composition by the insects and/or mollusca and the actual mitigation of the insects and/or mollusca, e.g. Fire Ants. The time between the collection of the product and the direct action of the pesticide on the immature stages and the queen is essential. The weaker (foraging ants) are not affected immediately and take the composition, e.g. bait, with the borates or borates and DE back into the ant mounds. Other fire ant mitigation products act immediately, unlike the action of the borates or borates and DE on the Fire Ants. Within the mounds, the queen ant and ants at immature stages of growth are fed the composition including the bait and toxicant (borates or borates and DE) combination. The slow acting borates are effective against the entire colony because of the specific action of the borates or borates and DE against organisms and protozoa in the gut of certain insects and/or the poisonous nature of borates an/or the abrasive action of the borates or borates and DE on the gut of the insect. It takes a few days for the borates or borates and DE to act depending upon environmental conditions. After a period of time, the organisms and protozoa in the gut are mitigated by the borates or borates and DE within the composition. Insects cannot digest complex foods. Since the organisms including protozoa act within the gut of the ant to break down the ingested food so it may be passed through the intestinal walls, the insect loses the capability to digest foods. As the organisms and protozoa are mitigated, the insects such as ants and orthopera are unable to digest food that is ingested thereby causing them to starve to death. Many insect species, including ants within the colony, feed on the carcasses of the dead ants thereby ingesting the composition within the body of the dead ants. The composition including the borates or borates and DE then acts to mitigate the organisms and protozoa in the gut of the ants feeding on the carcasses of the dead ants. As the organisms and protozoa in the gut of the scavenger ants are mitigated, these ants are also caused to starve to death. Eventually, the entire colony is effected. Applications on a ten day schedule over the same colony demonstrates that any residual populations left after a treatment also are mitigated. It is highly likely that the ants do not inhabit the same tunnels or mounds until all effects of the borates or borates and DE are gone. This may be some time because both the borates or borates and DE also possess an abrasive action that acts similarly to "broken glass". The exoskeletons may be pierced which drains all fluids from the insect resulting in dissication.

Borates and Diatomaceous Earth

The composition of the present invention is preferably broadcast (spread) over a target area infested with insects or mollusca using conventional methods. The composition includes environmentally acceptable baits as discussed, usually using the principal of the "Mother's Milk" with proportions of the protein, fat, carbohydrates, sugars, etc. necessary for the female of the species to reproduce. The baits as described may also be used with or without semiochemicals in combination with borates or borates and DE for the purpose of mitigating the target organism. The composition is preferably a powder, pellitized and/or encapsulated according to known processes and the combinations of the powder, pellitized and/or encapsulated bait and borates or borates and DE with or without semiochemicals that can be broadcast on the target area. The combinations of the above mentioned powdered, pellitized and/or encapsulated bait and borates or borates and DE have been shown to provide improved results over currently used compositions and systems while having a much less detrimental effect on the environment. The granulated (including pellets), powdered, and/or encapsulated combination is more easily handled than the commonly used corncob grit baits of today. For example, the micro sized granules and encapsulated product require use of conventional application systems while corn cob grits require a specialized application apparatus.

The use of the point source concept is in contrast to the prior art method of spraying an area using insecticide indiscriminately over all the components of the environment. The public feels this method is undesirable as it can cause trauma and/or death to beneficial organisms if broadcast treatments include some of the more toxic insecticides. The use of corncob grits with other low toxicity insecticides is not detrimental. However, the use of the composition of the present invention in the same matrix provides an even greater margin of safety to man, animals and the environment over currently used alternatives. Alternatively, corncob grits may also be used as an attractant, containing the borates or borates and DE of the composition therein. However, tests have shown that granulated and encapsulated formulations of the composition of the present invention provides superior performance to the corncob grits.

An example of a pest that has caused hundreds of millions, if not over a billion dollars of damage over almost thirty years in the United States is the Fire Ant (*Solenopsis invicta*). Food and feed crops, home and garden, livestock and other environments have been greatly disrupted by this pest. The bite of the fire ant is a public health problem. In fact, numerous human deaths have been attributed to the bite of this insect and complications resulting therefrom. Furthermore, calved cattle on the range are routinely killed by Fire Ants. Farming is disrupted in fields with high populations of the pest because of damage done to the farmer's equipment from the mounds. Urban areas and suburban yards are infested making it impossible for children or pets to play outside unless pesticides are used to lower Fire Ant populations.

The present invention mitigates not only this important pest but also several other pests which cause both economic consequences such as grasshoppers, crickets, locust and many other insect and also mollusca pests. The same principles of bait and kill will be applied using the described borates or borates and DE with a special "Mother's Milk" formulation.

The composition of the present invention uses combinations of the following components:

A. Borates
  1. Disodium Octoborate Tetrahydrate and other closely related sodium salts of borates;
  2. Boric Acid in special hydrated liquid formulations;
  3. Other borates including all the different salts such as sodium, calcium, etc. including hydrated and dehydrated forms such as calcium borate;
B. Diatomaceous Earth (DE), including silicon dioxide combinations with gels or other formulations. The purest form of DE has proven to be the most efficacious;
C. Baits (fructose, lactose, sucrose, protein, carbohydrates, fats, starches, etc. used singly or in combinations). As discussed the "Mother's Milk" formulation using the same properties of nutrients found in certain whey have proven to be the most effective attractants.
  1. Whey and other dairy products that are reinforced with the nutrients bringing the product to the discussed specifications;
  2. Manure, such as from cattle, hogs, sheep, chicken, etc. that is reinforced to with the proper nutrients such as fats, protein, sugars, etc.;
  3. Manufactured or processed products by themselves or reinforced as discussed in the "Mother's Milk" strategy using:
    a. dog and/or cat food;
    b. fats, oils and/or tissue from animal and fish rendering manufactured and processed to specification of the formulation of the present invention;
  4. Sugar and/or by-products of sugar production from sugar cane, sugar beets and other such sources of sucrose;
  5. Fruit production by-products from processing plants and other products from fruit production;
  6. Vegetable proteins, oils and sugars from processing plants;
  7. Other attractants utilizing plant or animal by-products;
D. Semiochemicals for mitigating a pest by attracting, repelling or congregating insects, mollusca or other organisms (optional); and
E. Other pest mitigating products including biopesticides such as NEEM or citronella (optional).

Another unique concept concerning the present invention is that waste and other products classified as toxic by the Environmental Protection Agency (EPA) can be used as baits in the composition of the present invention in a manner which is environmentally acceptable and useful in mitigating pests when combined with borates and/or diatomaceous earth.

In addition, the present invention incorporates two low to no toxicity products of relatively low cost allowing for the production of a pesticide which is more affordable by the general public.

Feed Through and Bolus Concept

The composition of the present invention uses non-toxic pesticides with feed or as a bolus (large slow release pill device). The pesticide becomes part of the digestive process and becomes part of the composition in the manure of animals. Animals that excrete the pesticide with manure will aid in lowering pests. This process involves mixing the pesticide with the food of the animal and, when eaten by the animal, passes straight through the digestive system of the animal in an unaltered state. Insects, including flies such as the face fly, horn fly, common house fly and Fire Ants use the manure as food and the pesticide destroys the insects as described previously.

Alternatively, the composition is formed into a bolus. The bolus which has a heavy substance such as iron oxide and a slow-release formulation which is deposited into the gut of the animal using the ball and gun method. The borates or borates and DE allows a continual flow of the pesticide that passes through the animal in an undigested state. Upon digestion of the food with which the composition is mixed in the case of the feed. Though the composition becomes mixed within the manure and deposited as a point source upon excretion of solid waste by the animal. The bolus acts on the same principal but becomes part of the manure because of the slow erosion of the bolus in the animals stomach. The depositing of the borates or borates and DE in the manure in this manner acts a point source for attracting the target organisms such as insects and/or mollusca. A point source is thus formed in each place where an animal within the target area deposits a pile of manure. This method has been demonstrated using only DE for flies, but not borates or borates and DE against flies and Fire Ants.

The components of the manure attract the target organism such as the Fire Ant and flies to the manure pile. The fire Ants pick up the borates or borates and DE and manure, carrying it back to the mound in which they reside. The composition including the borates or borates and DE is fed to the queen and immature stages of Fire Ants for example or flies in the immature stages of development. The borates or borates and DE within the composition eventually act on the queen and immature insects by mitigating organisms and protozoa in the gut of the ants or acts as a stomach poison or abrasive in the insect's gut. Without the organisms and protozoa in their gut to digest food, the ant is unable to be nourished by ingested food which remains undigested in their gut. Ants devour their dead, the borates or borates and DE remain unchanged in the gut of the dead ants. Therefore, the ant will thus eventually starve as food remains undigested in their gut. The entire colony is eventually mitigated as the remaining insects feed on the bodies of the dead insects containing the borates or borates and DE of the composition.

The present invention provides considerably improved results from the prior art simply by mitigating the ant outright without the ant being able to return to the colony. In addition, other pesticides repel the ants and the described composition attracts the ants. These improved results include improving the efficacy of the product by substituting borates or using borates in combinations with DE. The use of borates either alone or in combination with the DE expands the range of insects on which the prior art is effective beyond only flies to include numerous insects and organisms such as ants (specifically Fire Ants) in broadcast applications outside of confined areas such as houses, barns, etc. into the fields, lawns, etc.

Feed-Through

Borates are also essential to the health of the animals. The composition of the present invention including borates or borates and DE which may be mixed with food of the animal thereby supplementing the diet of the animal with necessary minerals. The mixing of the borates in the cattle food as a supplement is necessary when the soils do not contain enough boron and plants growing on the soil do not uptake enough of boron. The amount of borates mixed with the food is regulated by the present invention as excess boron can cause some symptoms in the animals, but are tolerated even when animals graze land with extremely high concentrations of borates.

The borates within the composition are fed with the prepared food and act to mitigate the parasites within the gut of the animal (Vermifuge) thereby boosting the meat and/or milk production of the animal.

The borates or borates and DE do not change significantly in the stomach of the livestock and pass through to become part of the manure. The flies that bother animals (e.g. face fly, horn fly and the house fly) reduce the body weight of animals and lower milk production. Therefore, the formulation aids in both the vermifuge (mitigating parasites in the animal's stomach) and feed-through which reduces the number of nuisance flies that breed in the manure. Fire Ants also use manure as a favorite food source.

Combining the borates and DE is synergistic (provide higher efficacy at lower rates than either borates or DE alone). Using a combination of borates and DE provides increased efficacy when the composition becomes a point source as a manure patty after being deposited by the animal.

Rates for Feed-Through

The most effective and thus preferred rate of DE is substantially 1% total feed with the lower end of the effective rate for borates being substantially 0.1%. The effective rate for the combination can be as low as substantially 0.5% DE and substantially 0.05% borates. A reduction in the rates of both DE and borates lowers the chance of exposing the animal to any excess of micronutrients that may have a toxic effect on the animal. No adverse affect is expected at even the higher rate.

The borates have demonstrated efficacy in mitigating populations of Fire Ants in trials conducted by the inventors. Animals fed borates or borates and DE combinations can also be used to mitigate a wide range of insect pests when used in livestock food, including but not limited to:

(1) Flies, e.g. house flies, face flies, horn flies, etc.;
(2) Fire Ants;
(3) Parasitic worms, including nematodes; and
(4) Harmful protozoans and other harmful organisms.

Summary of Feed-Through Environmental Effects

The feed introduced into the stomach of the animal with the composition containing the borates or borates and DE mixed therein passes through the digestive tract of the animal and is combined with the manure. The manure and composition are deposited as a point source upon excretion by the animal. The organic components of manure are gradually incorporated into the soil and recycled by plants. The amount of borates or borates and DE in the manure are beneficial to the soil and plants growing therein. Borates and DE are used in soil supplements and thus cause no harm unless applied at rates much higher than those disclosed and recommended by the present invention. The borates or borates and DE which is not taken away by the target organism are also gradually incorporated into the soil and aid in the growth of the plant life in the target area. The present invention limits the amount of the borates or borates and DE that would reach aquatic areas since the products in manure are slowly released and only as the manure degrades. The borates bind with the soil and thus little to no run-off or downward movement occurs. The DE does not degrade and is not of any environmental concern.

The present invention greatly reduces the amount of pesticides used to control insect pests such as flies and Fire Ants. Manure piles with topical applications of borates or borates and DE show efficacy without the use of broadcast treatments over the entire area. The present invention is effective in mitigating various fly species including over 80% efficacy in the mitigation of house, horn and face flies. The present invention has shown almost 100% mitigation of Fire Ants and all the above mentioned species of flies using a combination of borates or borates and DE as discussed above incorporated into the manure immediately after the manure was deposited. Furthermore, no insect resistance to the composition containing borates or borates and DE is expected to develop.

The present invention illustrates that feed through using borates or borates and DE provide excellent results. The efficacy of the present invention has been recorded in carefully controlled studies. Various concentrations of borates or borate and DE combinations were fed to various livestock and the manure produced by the livestock were subjected to Fire Ants and fly species in caged studies to determine efficacy. The efficacy of the formulation is not significantly affected by the process of feed-through.

The mitigation of Fire Ants and flies in live stock production areas caused by the use of the present inventive composition greatly increases the quality and quantity of the animals living in the area in which mitigation occurred. For example, Fire Ants in high populations are able to kill new-born calves in the field. Flies in high concentrations in dairy farms reduce milk production and cause weight-loss of cattle in holding areas. The use of the compositions of the present invention to mitigate these Fire Ants, flies, etc. in such areas greatly increases production with little to no adverse effects on man or the environment.

The environmental Protection Agency (EPA) label for the composition of the present invention will be under category IV in the Precautionary statements. This is the lowest toxicity category. No other pesticide in use against Fire Ants carries this category.

When the composition of the present invention is broadcast using the method of feed-through, the side benefit of vermifuge is present at least to some extent. Vermifuge is a method for mitigating intestinal parasites, protozoans and other animals living in the stomach and/or intestines of animals. The mitigation of these intestinal parasites, protozoans and other animals improves the health of the animals to which the composition is fed and therefore increases the quality and quantity of meat, meat by-products, eggs, milk, etc. Vermifuge can also be used on other domestic animals such as pets (dogs, cats, pigs, etc.). When the composition is fed to the animal, it passes through the gut and acts on the organisms therein. The composition may be in a prepared food mix, mixed in with the food of the animal prior to eating or directly deposited in the stomach of the animal in the form of a large capsule using the ball and gun method. The use of borates and/or combinations of borates and DE (products) for vermifuge provides mitigation of many harmful organisms in the stomach and/or intestines of the animal such as nematodes, etc. with little to no adverse affect on the animal. The present invention lowers the number of adverse organisms in the stomach and/or intestines and can be used when the animals are diagnosed as adversely affected by intestinal organisms. The present invention may also be a specially formulated combination of borates or borates and DE with and/or without vermifuge medicines. The formulation with specific drugs can increase the effect of the drug(s) and/or increase the range of intestinal pests mitigated.

The use of the composition of the present invention with medicines also act synergistically since the DE acts as a mechanical abrasives breaking the exoskeleton (cuticle) and/or outer surface layers of other organisms such as nematodes. The borates act in much the same way and have the added mode of action as a toxin to protozoan and other organisms that inhabit the stomach of mammals. It is known that borates mitigate such organisms in the gut of insects. The combination of the medicines with the borates and DE thus provide improved results over the use of medicines alone.

The borate and borate/DE composition of the present invention mitigates the internal parasites and/or protozoa attacking the stomach of the animal. Certain internal parasites are mitigated and excreted. Upon mitigation and excretion of these internal parasites, the animal is healthier and provides more meats and meat by-products, eggs, milk, etc.

Exterior Treatment of Animals

The present invention also encompasses the methods of dusting and/or spraying livestock with borates or borates and DE combinations for the purpose of mitigating pest problems. Borates are known to mitigate fleas and ticks and are also used on pets (dogs, cats, etc.). The combination of the composition including borates or borates and DE with NEEM, Citronella and/or other products such as pyrethrum, artificial pyrethroids, etc. can also act as a repellent to many species of insects and mitigate these insect species that are not repelled. The borates or borates and DE composition of the present invention can be formulated in a powder, a mini granule or encapsulated with NEEM or Citronella or other products that have insecticidal value such as pyrethrum and/or piperonly butoxide. The NEEM, Citronella or other insecticides cause the granule to adhere to the animal. The presence of the composition of the present invention on the animal effectively mitigates fleas and ticks on the animal. The composition of the present invention is preferably formulated as a slow-release composition thereby giving long-term protection.

When the composition of the present invention is pelletized, a hydrophylic product may be added to the bait in certain treatment scenarios. The composition proves more efficacious with the addition of the hydrophylic product than formulations when dry. The moisture from rain or dew make the pellet or granule more palatable and therefore, more acceptable to the pest or organism in areas where little moisture is available through rain or irrigation.

Mode of Action

The composition of the present invention is slow acting. The slow action of the borates against cockroaches, ants, termites, and other insects allows the ingested borate to travel to the gut (stomach) of the insect such as the Fire Ant wherein protozoa and other organisms are mitigated thereby. The organisms in the gut of the insects break down the complex food chains and exist on some of the nutrients. Without these organisms in their gut, ingested complex foods cannot be broken down into simple basic components such as sugars, carbohydrates, and proteins that can pass through the gut wall into the insects' system. The insects cannot break down the complex foods without the aid of the organisms in their gut. As these organisms are mitigated over the course of a few days to a week, the insect becomes more lifeless as time passes (moribund), stops eating and breeding and is of little threat to the environment. The simple foods that were available when the protozoa were breaking down the complex foods remain undigested in the gut of the insect. The insect then dies of starvation which generally takes a few days to more than a week as it cannot break down the food into a useable form.

Boron, when added in the right concentration to the composition, may be passed from one generation to the next in insects such as the fire ant. The brood (immature ants) are fed regurgitated food including the borates thereby causing death to the next generation. The ants also cannibalize their own, eating the carcasses of the dead. As the borates do not degrade, the toxin in the ant or other such insect carcasses mitigated by the borates is passed to the living ants through the body fluids. The death or morbidity effect of cannibalism continues until the dilution of the borates achieves a no-effect level.

The slow action of the borates may be considered to be a negative aspect of using the borates. However, this slow action enhances the positive result of its effectiveness against not only the present generation, but also succeeding generations. An insecticide can mitigate the target organism immediately and thus demonstrates good results in the short term. However, as in the case of Fire Ants, the queen and immature insects still thrive and the colony survives. The present invention includes a slow acting pesticide that allows the insect to take the composition back to the center of the colony and mitigate the entire colony over time. An integrated strategy for providing faster results is to apply the formulation and wait at least six hours for all the bait to be taken back to the mound. After the six hours, a "fast kill" treatment should eliminate the ants on the surface still foraging while the bait and slow acting borates or borates and DE mitigate the ant stages in the mound.

Many currently known and used insecticide formulations spoil or degrade rapidly because of the effect of bacteria or fungus action on the chemical itself and/or the other components of the formulation. Borates are unique due to the fact that the chemicals act as a low-level bacteriacide, fungicide, and algicide especially in dry formulations with sugars, carbohydrates, proteins and fats where the formulation is susceptible to attack by such organisms. If the composition containing borates of the present invention is kept dry, the composition is protected to a higher degree than the other currently known and used insecticide formulations.

Borates, as used in the composition of the present invention, are in solid form and easily incorporated into bait formulations using a single component or in combinations of starches, sugars, carbohydrates, fats, proteins and/or semio-chemical attractants. The borates are soluble at low levels but do not need to be in a liquid form.

Borates are not highly soluble and bind with the baits. This makes leaching of the borates from the formulation and into the environment more unlikely. If borates should separate from the bait, the borates characteristically bind with organic material in the soil and do not present the problem of leaching into the ground water table even at high rates. Boron (borates) is an essential element in the growth of plants and is added as a supplement in agricultural areas to promote vigorous growth at rates of over two pounds per acre. This micronutrient is in most major plant growth formulations that contain plant extracts high in boron.

At high rates borates can be phytotoxic. However, the expected use rates of the borates in the formulations of the present invention vary from substantially 0.05% to substantially 5.00% or higher. At these rates the total amount of borate will not exceed the equivalent of substantially 2.0 pounds active (boric acid equivalent or BAE). In addition, the borates are bound to the bait and spread as point source pellets including granules, encapsulated product and corn-cob grits. This further reduces the amount of available BAE to the environment.

The borates measured as BAE's have shown phytotoxicity to certain sensitive species of plants at extremely high rates on the order of substantially 1.0 ppm available BAE. However, the BAE available to the roots of sensitive plants is considerably lower because of the factors previously discussed. The borates in a point source are pelletized (including granules) and/or encapsulated and then broadcast (spread) over an area with spacing between the point sources. For these reasons, the chances of phytotoxicity of even sensitive plants and the possibility of excess borates in the ground water is highly unlikely to almost impossible.

Diatomaceous earth (DE) including silicon dioxide is used in many plant fertilizers as a micro nutrient. Many times DE is used alone in crop areas to promote more vigorous growth. There are no adverse effects noted in the use of DE, even at high rates. DE is a solid and is easily incorporated into the bait with the borates. The leaching of borates have no adverse effects. For example, DE is used in swimming pool filters and other devices to purify water. Even at high rates, DE is not phytotoxic to plants and is used in many plant growth formulations to add micronutrients to the formulations.

The baits used as attractants in the composition of the present invention primarily consist of waste products of agriculture and industry, some of which are considered toxic in nature. The composition of the present invention thus is able to make use of these wastes in a safe and beneficial manner. For example, whey is a by-product of the dairy industry and has shown extremely good activity. The investigators have noted a relationship between the extremely attractive baits and the vital nutrients, minerals and basic food components such as simple sugars, carbohydrates and fats needed for the target insect's vitality and reproductive needs.

Numerous benefits are obtained by using the composition of the present invention as point source insecticides and molluscacides. One such benefit is that the composition of the baits used in present invention is made from products generally considered hazardous waste which are converted into an environmentally acceptable product. The composition of the present invention for mitigation of such pests as Fire Ants thereby providing great benefits. These benefits include but are not limited to the use of wastes such as whey, manure, and other by-products of agriculture including processing waste by-products of fruit, vegetable, meat production and many other processes which are difficult to dispose of and require special handling. Such wastes are utilized as bait in formulations of the present composition that are environmentally acceptable and can be disposed of without special measures.

The use of low rates of borates and/or diatomaceous earth (DE) in the composition of the present invention helps the environment by improving plant growth. Both products have known benefits to plants and animals.

The highest rates contemplated by the present invention for both borates or borates and DE do not cause phytotoxicity or pose any problems to ground water. Thus, the use of the composition of the present invention will not harm the water of the territory in which the present invention is applied or broadcast.

The composition of the present invention use relatively low cost components for insecticides and the bait formulation is economical and available. Complex conventional methods of manufacturing the products may be used. However, newer methods of formulation can also be utilized. Mitigation of any adverse organisms in the waste (whey and manure as an example) are not easily destroyed by known methods economically except when the waste is heated to high temperatures or other processing is used that lowers animal and plant oils and other volatile substances needed as attractants in the bait. New methods tested by the inventors of the present invention achieve the same results without heating. Both new and old methodologies are sufficient to provide a point source pellet, granule, encapsulation or microcapsule for purposes of this invention.

No adverse by-products of any of the above methods of manufacture result in adverse effects to man or the environment. Thus, manufacture and handling of the composition produced in accordance with the present invention and application of the present invention will not require any special procedures for handling wastes from manufacture of the composition.

The composition of the present invention uses only low toxicity pesticides that do not cause harm to those manufacturing distributing or using the products when following label directions and lessens the effect on man and the environment in comparison to currently available products and procedures.

An integrated program using the compositions and methods of the present invention can greatly reduce the over-all effect of pests of live stock, croplands, nuisance pests of public health concern. Domestic pets can also benefit from the use of topical applications and/or vermifuge and/or feed-through of the present invention.

The use of powders, pellets and/or encapsulated forms of the composition of the present invention for the purposes of broadcast (spreading) application incorporate some baits that are considered toxic wastes and in some cases, hazardous wastes in such a manner as to make the wastes useful and beneficial. The present invention uses a bait comprised of conventional products as well as waste products including by-products, some of which are considered toxic waste by the EPA. The waste products are processed to produce a useful non-hazardous formulation for use in attracting and control of certain pests of economic importance.

The borate or borate and DE combined with the bait provide micro-sized point sources for treatment by broadcasting (spreading) rather than providing complete coverage with a pesticide. This type of treatment of an area decreases the detrimental environmental effects caused by the use of a more toxic pesticide broadcast over the entire area. The elimination of the negative environmental effects by the present invention allows for an integrated approach to pest management as the borate or borate and DE combined with the bait are more host specific and are not broadcast. Thus, most beneficial parasites and/or predators of the insect or mollusca are able to survive and therefore have a greater impact on the target organism. The affect of keeping a balance of the complex biocontrol program in place while lowering the impact of the target organism (such as the fire ant) lower the number of treatments necessary to achieve mitigation. This strategy benefits both man and the environment.

The advantage of using the bait and mitigate system of the present invention is that the target insect selects the bait and carries the borates back to the colony or concentration of pests. The parasites and/or predators are interested only in the target insect. Therefore, the bait and mitigate system does not effect the parasites and predators because this group is usually host specific. Also, as the composition of the present invention does not attract the parasites and predators, it is not ingested by these organisms. As populations of beneficial insects increase, the population of the target insect is more likely to come into balance with a concurrent reduction of the target pest and the less likely need for a broad spectrum pesticide(s).

The composition of the feed-through and ball and gun use borates or borates and DE and/or animal drugs.

The composition of the present invention may be prepared in the following manner and fed with animal food for mitigation of insect pests in manure:

For Feed-through
(1) In a powdered, pellet or encapsulated form for mixing with feed;
(2) In a powdered, pellet or encapsulated form in a prepared mixer with feed; and/or For the Ball and Gun Method
(3) Prepared as a bolus for application using a Ball and Gun method into the stomach of cattle and/or other animals. The bolus, a large capsule, is inserted through the mouth of the animal using a rod and lodged in the stomach of the animal (usually a ruminant such as cattle). The bolus is a slow-release product that degrades over a period of time (up to or more than three months). The product is continuously present in the stomach over the period of time during which it degrades and more products are degraded from the bolus when stomach acids, etc. are activated during feeding.

For Topical Application
a. Borates (including boric acid) with or without DE and possibly including NEEM, citronella or other insecticides for placement over and adhering to the coat of the animal in order to repel or otherwise mitigate flies, ticks, Fire Ants, etc.;
b. Applied in powdered and/or liquid form over the coat of the animal with traditional applicators. Especially designed livestock shoots that activate the release of powdered and/or sprays by an electronic or mechanical trigger or other methods may be used in such shoots;
c. Micro-encapsulated product allowing for slow release and/or providing an adhesive to hold the product in place over a longer period of time than the powder and/or liquid sprays; and
d. Time released micro sized granules may be used to provide long-term control.

There are no risks associated with use of the present invention when used to mitigate populations of pests. The present invention only incorporates low toxicity (category IV, lowest toxic label by the EPA standards) products that have little to no effect on man or his environment. The possibility does exist that the bait with the borate or borate and DE could mitigate some non-target beneficial insects or mollusca of the same family. However, the impact of mitigating the population of an insect like the fire ant is that the native species are no longer driven from their territory or mitigated by the target insect. In areas having high density populations of Fire Ants, all insect species and even mammals are unable to occupy the same space as the areas infested by Fire Ants.

Any adverse effect of the use of the present invention should not have any additional impact to areas where high densities of the fire ant reside. Upon establishing control or elimination of the target pest using the composition of the present invention, use of the composition may be stopped and the natural balance which existed in the space occupied by the Fire Ants (for example) will return to normal.

EXPERIMENTAL RESULTS

The following are the results obtained for tests performed to establish the effectiveness of the composition of the present invention on Fire Ants.

Attractants

The following components were tested either alone or in combinations for their ability to attract Fire Ants:
1. Cow manure dropping in an infested area;
2. Pelletized cow manure;
3. Milk;
4. Powdered, fresh and pelletized whey;
5. Sugar solutions of varying concentrations;
6. Raw fruit and vegetables of various kinds and concentrates;
7. Various soft drinks containing sugar;
8. Bacon and other raw meats;
9. Vegetable and animal oils, both in liquid or solid;
10. Dog and cat foods in bags, cans, or packaged in some other manner;
11. Corn or other vegetable products in the form of meal, syrup, cracked, particles and flakes and other particles;
12. Wheat and rice as bleached and unbleached, flower or granules;
13. Millet seeds whole and crushed;
14. Sunflower seeds whole, crushed and with various vegetable oils added;
15. Microcapsules of whey and other materials, made to hold various, foods, etc.; and
16. Capsules made of various vegetable water, sugar, starches, proteins, etc. that contain the bait and/or borates and/or DE.

Summary of Results on Attractants

The order of attractiveness for each product was highly dependent on the amount of moisture contained in the test substance and the amount of simple sugars, carbohydrates and/or proteins in the formulation. It was found that the raw agricultural products, including animal wastes such as fresh manure are the most attractive. All fresh fruits and vegetables are good attractants to most insects and/or mollusca species.

Disodium octoborate tetrahydrate (DOT) and other borate salts (including calcium salts) were incorporated in a few of the subject products and were readily accepted by the Fire Ants when incorporated with the baits tested. Boric acid was also included in the study. The data demonstrated a high mortality (over 90%) rate for Fire Ants and evacuation of the ants from mounds in every test conducted using raw agricultural wastes and commercially available baits.

Fire Ants (Example)

Acceptance of processed wastes such as pelletized manure demonstrated good attractive capabilities and efficacy although not as good as raw agricultural products and wastes such as fresh manure and whey. The efficacy of the processed animal and plant by-products was still high (90% mortality or higher), but the ants were not as aggressive in their pursuit of the processed product. Other mechanisms may be working, but it is suspected that the unprocessed product may have certain volatile components that are highly attractive and not present in the processed baits.

The preliminary studies were conducted in North Central Texas, the high heat and no rain were contributing factors in the results. Studies conducted on a highly infested irrigated lawn produced much better attractiveness of the baits and caused more aggressive behavior in the ants toward taking product to the colony. The results of further studies in varying climatic conditions are presently underway and appear promising in conditions where rainfall is higher. Based upon these results there is evidence that Fire Ants can be controlled and/or eradicated in isolated infestations using the composition and method of the present invention.

The upper and lower limit of borates incorporated in the baits have been examined on a small scale (individual mound) basis. The break-off of efficacy of the product appears to be at substantially 0.1% of the formulation and the Fire Ants still accept substantially 5.0% borates in the formulation. The use of slow release additives to granules and microcapsules can time-release the product making the bait/borate viable at selected intervals. The inventors suggest a cycle of immediate viability, ten (10) days and twenty (20) days. Each batch can be run individually and combined in one package to allow for availability of the bait and toxicant over a period of time. The one treatment would assist in a longer treatment time frame.

The baits used and percentage of borates or borates and DE vary with the target insect or mollusca. Our preliminary data shows an acceptable formulation to be near substantially 0.05% borates (DOT) of the formulation for first generation control to substantially 1.0% for control into the second generation of Fire Ants. The inventors have determined that a concentration of over substantially 1.0% are effective and believe that second generation effects can be realized at levels as low as substantially 1.0% on future generations of the Fire Ant, for example. However, the 5.0% borate or borate and DE have shown no repellency by the ants and the affect of having a reservoir of the toxins in the mound appear to keep the mound from revitalizing for longer periods of time.

METHODS OF EVALUATION

Fire Ants

Mounds were selected of varying sizes measured in diameter:
1. Small mound (1 inch to 6 inches)
2. Medium mound (6 inches to 3.0 feet)
3. Large mound (3.0 feet and larger)
4. Control When possible, isolated mounds were selected. It was found that all mounds in a heavily infested area are interconnected making isolated observations difficult. The inventors observed heavy deposition of ant carcasses at the entrance to mounds probably connected to the treated mound. It is evident that the bait and borates are distributed through the mound system and broadcast treatment would allow equal treatment of an area and therefore impact the entire mound system.

The formulations were tested individually at different sites:
1. Standard was one level teaspoon for a small mound, two for a medium mound and three or more for a large mound; and
2. Volume vs. weight was noted.

The following data was collected for each site:
1. Location
2. Data and time of application
3. Observation are conducted at:
   a. One hour;
   b. Four hours;
   c. Twelve hours;
   d. One day;
   e. Two days;
   f. Four days;
   g. Eight days;
   h. Sixteen days; and
   i. Intermittent observations based upon climatic conditions.

4. Weather data collected include:
   a. Temperature;
   b. Humidity;
   c. Rainfall (time of day and extent); and
   d. Wind speed and direction
5. General observations The time of application is preferably near evening (5 p.m. or later) or early morning (5 a.m. to 9 a.m.). The dew, if present, helps in the palatability to the Fire Ants of the point sources because of the hydrophilic nature of the formulation as indicated by the preliminary studies.

RESULTS AND DISCUSSION

The most promising bait consists of 5% DOT, 1% DE and 96% whey in either a powdered and/or granulated formulation. A bait containing whey or other combinations including but not limited to 20% whey, 5% DOT and 75% manure in granule (pellitized) or encapsulated form are also effective in mitigating fire ant populations to an acceptable level and possibly elimination of small isolated infestations in previously non-infested areas using time release delivery systems of varying lengths. Other formulations that can be commercialized include manure from cattle with DOT at substantially 5.0% using the new and innovative methods of pelletizing.

Substitution of 5% calcium borate for the DOT also demonstrated superior performance with whey.

Other formulations using whey as an encapsulating agent with a previously described bait showed promise as the outer shell is composed of whey (alone an attractant). Other encapsulation products have similar performance capabilities.

Formulations containing any of the above proposed baits in combination with borates or borates and DE will provide a measure of efficacy. The most economical formulation matched with acceptable efficacy can be marketed.

The use of botanicals as a substitute for the borates is also effective in mitigating the population of the target insect. Juvenile hormones and/or chitinase inhibitors are also an acceptable substitute for the use of borates.

Area Wide Treatment Strategy Using the Composition of the Present Invention

The present invention is effective as a part of an integrated pest management system. The use of broadcast insecticides including the borate or borate and DE granules and in encapsulated bait formulations fit nicely into an area-wide program in a livestock production area. As previously discussed, the borates or borates and DE are environmentally acceptable with little to no adverse effects to man or the environment during manufacture, application or post-application while using the invention.

From the above description it can be seen that the composition of the present invention is able to overcome the shortcomings of prior art devices by providing a composition which is able to mitigate a population of insects and/or mollusca, especially Fire Ants, within a target area without causing damage to persons or the environment within the target area. The composition is not toxic to both the environment or humans. and includes borates combined with an attractant. The composition is able to pass through the digestive tract of an animal inhabiting a target area, the composition being deposited with the manure of the animal as a point source in the target area for attracting the insects and/or mollusca. The composition may also include diatomaceous earth combined with the borates to add a residual affect noted in testing. Any of the composition not ingested or carried away by the target insect is able to fertilize the ground on which it is deposited thereby increasing the fertility and production of the ground. The composition may also be combined in the feed of an animal and able to mitigate parasites and harmful organisms within the gut of the animal upon ingestion thereby improving the health and increasing the production of the animal. Furthermore, the composition of the present invention is simple and easy to use and economical in cost to manufacture.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A composition for mitigating insects and/or mollusca comprising a mixture of whey and a hydrated borate salt, wherein said hydrated borate salt is in an amount ranging from 0.1% to less than 5% by weight for use outdoors and specifically in areas infested with insects and/or mollusca.

2. The composition of claim 1, wherein the hydrated borate salt is selected from the group consisting of Disodium Octoborate Tetrahydrate, hydrated sodium borate, and hydrated calcium borate.

3. The composition of claim 1, wherein the mixture is in pelletized form.

4. The composition of claim 1, wherein the mixture is in encapsulated form.

5. The composition of claim 3, further comprising animal feed for combination with the pelletized composition, wherein said composition is digested by an animal with the animal feed and the composition is deposited within a manure patty as a point source within a target area inhabited by the insects and/or mollusca to be mitigated.

6. The composition of claim 5, wherein the composition is formulated as a bolus, said bolus being deposited by a ball and gun process into a stomach of the animal.

7. The composition of claim 6, wherein said bolus erodes slowly within the stomach of the animal thereby allowing the composition to be deposited as a point source manure patty in manure of the animal.

8. The composition of claim 3, wherein said composition further includes a hydrophylic product thereby the composition.

9. The composition of claim 1, wherein the composition includes 0.1% hydrated borate salt by weight.

10. The composition of claim 1, wherein the composition includes 0.5% DE (diatomaceous earth) and 0.05% borates.

11. The composition of claim 1 further comprising at least one of Diatomaceous Earth (DE), Vegetable proteins, vegetable oils, animal oils, sugars, manure, semiochemicals, and biochemical pesticides.

12. The composition of claim 11, wherein the biochemical pesticide is selected from the group consisting of NEEM, citronella and pyrethrum.

13. The composition of claim 12, wherein said NEEM, citronella or pyrethrum in said composition aid in application of said composition to the skin of an animal for mitigating fleas, ticks and other livestock pests on the animal.

14. The composition of claim 11, wherein said diatomaceous earth is present in an amount ranging between 0.5% and 1% by weight.

15. The composition of claim 1, further comprising an attractant selected from the group consisting essentially of fructose, lactose, sucrose, protein, carbohydrates, fats starches.

16. The composition of claim 3, wherein the composition further includes animal drugs.

17. The composition of claim 1, further comprising diatomaceous earth and wherein the composition is in the form of a bolus for deposit directly into a gut of animal, said bolus being combined with manure produced by the animal and deposited as a point source within a target area inhabited by the insects and/or mollusca to be mitigated.

18. The composition of claim 4, wherein the composition further includes animal drugs.

* * * * *